US006231579B1

(12) United States Patent
Castro Netto

(10) Patent No.: US 6,231,579 B1
(45) Date of Patent: May 15, 2001

(54) PADLOCK TYPE MARKING SEAL AND APPLICATOR FOR APPLYING PADLOCK TYPE MARKING SEALS

(75) Inventor: Eduardo De Lima Castro Netto, Rio de Janeiro (BR)

(73) Assignee: ELC Produtos De Seguranca Industria Comercio Ltda., Rio de Janeiro (BR)

( * ) Notice: Subject to any disclaimer, the term of this patent is extended or adjusted under 35 U.S.C. 154(b) by 0 days.

(21) Appl. No.: 08/945,907

(22) PCT Filed: May 3, 1996

(86) PCT No.: PCT/BR96/00017

§ 371 Date: Oct. 30, 1997

§ 102(e) Date: Oct. 30, 1997

(87) PCT Pub. No.: WO96/35201

PCT Pub. Date: Nov. 7, 1996

(30) Foreign Application Priority Data

May 3, 1995 (BR) .................................................. 9501886

(51) Int. Cl.[7] .................................................. A61B 17/00
(52) U.S. Cl. .............................. 606/116; 606/117; 40/301
(58) Field of Search ................. 292/307 A; 40/300–302; 156/DIG. 23; 24/326, 327, 704.1, 705, 453; 227/175.1–182.1; 119/856, 858

(56) References Cited

U.S. PATENT DOCUMENTS 3,400,479 * 9/1968 Anderson et al. ................... 606/117
3,712,655 1/1973 Fuehrer .
5,474,569 * 12/1995 Zinreich et al. ..................... 606/151

FOREIGN PATENT DOCUMENTS 2 540 069 8/1984 (FR) .

* cited by examiner

*Primary Examiner*—Glenn K. Dawson
(74) *Attorney, Agent, or Firm*—Smith, Gambrell & Russell, LLP

(57) ABSTRACT

A padlock type marking seal having a receiving body (2) with internal locking teeth (4) to receive the tip (9) of a loop of the seal that is integral with the body, and there being a marking tab (6) also integral with the body (1). In order to improve seal application, to ensure autopenetration into the material to be marked (e.g. meat), the tip is sharpened and there is a stop (11) on the loop, adjacent to and behind the tip so as to allow an applicator device to force the sharpened point to penetrate the material to be marked. The loop of the seal has a reduced thickness region defining a pivot point (8) with respect to the body, and the part (7) of the loop between the first end and the sharpened tip is substantially in the form of the arc of a circle. A reception cavity (3) in the body of the seal has an axis substantially tangential to the arc when the loop is pivoted about the pivot point, until its tip begins to enter said cavity. The applicator according to the invention is in the form of a pistol and is adapted to receive comb of seals. The applicator is operated pneumatically to: apply seals without the applicator element (39) having to penetrate the material to be marked; feed the next seal to the reception and application station (25); and cut the links (12) with the following seal before its application. The pistol is fired by a trigger and the operating sequence is controlled and effected by a remote control unit (15) comprising electronic control circuits (44) and pneumatic valves (16).

13 Claims, 4 Drawing Sheets

PADLOCK TYPE MARKING SEAL AND APPLICATOR FOR APPLYING PADLOCK TYPE MARKING SEALS

TECHNICAL FIELD

The present invention relates to padlock type marking seals which are used to mark any type of material capable of being pierced by the tip of the seal lock. For example, cloth, live fish, cattle (through the ear), meat and the like may be marked using this type of seal.

BACKGROUND ART

There are two principal disadvantages encountered when using the seals and applicators of the present state of the art:

Firstly, it is difficult to close the seals using mechanical applicators, due to the fact that there is normally only one pivot or fold point of the "loop" of the padlock, and the locking tip of the "loop" must enter the locking capsule in the body of the "padlock" in a substantially linear manner. The shape of the seals known in the state of the art is not very well adapted to operate in this way and there is a tendency, upon application of the seal, for it not to close properly. In addition to this, the marking operation becomes slow; and Secondly, it is normally a needle portion of an applicator that penetrates the material to be marked, drawing the tip of the "loop" with it. This means that the applicator imposes design requirements which are difficult to comply with when aiming for simplicity of operation. As a result of this, mechanical applicators, as a rule, are not practical. In the majority of cases they can only be used for application of a single seal, not being provided with means for carrying a number of seals, so that multiple application of the seals at an accelerated rate can not be carried out.

Padlock seals for other purposes are known, such as that shown in U.S. Pat. No. 3,712,655 which discloses a security, tamper-proof having the general appearance of a conventional padlock. The loop or hasp of the padlock is flexible and generally hoop shaped terminating in a free end in the form of a snub nosed locking tip designed for being manually guided into a locking cavity in the body or base of the seal. Behind the locking tip of the hasp there is a protuberance or enlargement for manual gripping at the time of inserting the tip in the locking cavity.

Applicator devices are also known for the type of tie seal that is used for fixing price is tags to garments or the like. An example is to be found in FR-A-2 540 069 which discloses a pistol having jaws into which a loading mechanism inserts the locking tip at one end of the tie into an outer end of one of the jaws and the locking cavity at the other end of the tieinto an outer end of the other jaw. Rotation of the jaws about a fulcrum by means of a trigger mechanism forces the locking tip linearly into the locking cavity, a price tag or the like and a part of the garment to which it is to be fixed being interposed between the jaws.

OBJECT OF THE INVENTION

The principal objects of the present invention are to provide a padlock type marking seal which is adapted to be easily applied and also to provide a marking seal applicator that is practical, fast and, in the preferred embodiment, capable of carrying "combs" of seals that can be applied in sequence.

SUMMARY OF THE INVENTION

According to a first aspect of the present invention a padlock type marking seal comprises a body defining a cavity having an internal locking formation, a preformed loop having a first end integral with the body and a second end in the form of a tip formed to cooperate with the internal locking formation of the cavity, the loop being flexible so as to permit said tip to enter the cavity and to become locked in said formation, and a marking tab integral with the body, there being a stop on the loop, adjacent to and behind said tip. The seal is characterised in that:

the tip of the loop is sharpened so as to be capable of penetrating the material to be marked, the first end of the loop is connected to the body by a region of reduced thickness to define a pivot point and the part of the loop between the first end and the sharpened tip is substantially in the form of an arc of a circle, the cavity having an axis substantially tangential to said arc when the loop is pivoted about said pivot point until its tip begins to enter said cavity.

Preferably, said arc is substantially semicircular.

In the preferred embodiment of the present invention, the sharpened tip is in the form of a head connected to the rest of the loop by a neck, there being—in order to reinforce the tip and thereby prevent it from flexing as it penetrates the material to be marked—a reinforcement in the form of a connecting rib in the vicinity of the neck.

The advantage of the seal of the present invention lies in the fact that, when the sharpened tip of the seal is placed against the material to be marked, pivoting of the loop causes the tip to enter the surface of the material almost rectilinearly, penetrating and then turning inside the material, in a way similar to a curved suture needle, finally to exit from the same surface that it went into and then directly to enter the cavity of the seal to cooperate with the locking formation.

As in known seals, the locking formation is provided advantageously with one or more—normally three—internal teeth in said cavity. In this way, the reinforcement rib on the neck, between the sharpened tip and the remainder of the loop, can enter the space between two of these internal locking teeth in the cavity of the seal.

Apart from this, the stop behind the sharpened tip of the loop allows an applicator device to be used, the forward point of which does not need to effect penetration of the material to be marked, simply following the sharpened tip of the seal, which is itself used to effect penetration.

According to a second aspect of the present invention, a marking seal applicator for applying padlock type marking seals in which the tip of a preformed loop of the seal is sharpened so as to penetrate the material to be marked and, upon exiting the other side of the material, to enter into a locking cavity of the seal, said applicator including a seal application and reception station, a seal applicator device at said reception and application station for rotation about a pivot point and actuator means for inserting said tip into said locking cavity is characterised by comprising:

a feed guide defining a pathway for feeding a a series of interconnected seals towards said reception and application station, a region of the reception and application station being open to the feed guide so as to enable a marking seal to pass from the guide into a reception and application position within said reception and application station;

a movable stop, displaceable between an open position, spaced from the reception and application station, and a seal application position in which the movable stop is located in said open region to align and support that portion of the seal defining said locking cavity; and a first actuator, associated with the feed guide, for advancing the sealsincrementally along the guide towards the reception and application station;

said actuator means comprising a second actuato, associated with said movable stop, for displacing said stop between said open and seal application positions, and a third actuator, associated with said applicator device, for imparting rotational motion thereto, between an open seal position and a closed seal position, and for returning said applicator device to said open seal position;

said actuator device including an actuator element having an inner curved surface substantially corresponding to the shape of outer surface of said preformed loop of a seal located in the reception and application station, with the sharpened tip of the loop of the seal directed away from the applicator device, the applicator device cooperating with the loop so as to move together with the applicator when it is rotated about the pivot point by said third actuator.

Preferably the first, second and third actuators comprise respective first, second and third pnuematic cylinders with return springs. The applicator may also include a cutting mechanism, adjacent the open region of the reception and application station, for cutting weakened links between adjacent seals in said series, the cutting mechanism being associated with the second actuator so as to effect cutting simultaneously with displacement of said movable stop to the seal application position.

In the preferred embodiment, the applicator in the form of a pistol with a trigger for starting an operating sequence of the actuators has a remote control for controlling the application of pneumatic pressure to said cylinders and an electronic circuit programmed to open and close the valves according to the actuator operation sequence, the circuit being activated by the trigger of the pistol. This sequence of operations occurs as follows:

a) the third actuator rotates the applicator device from its open seal position into the closed seal position and soon after back to the open seal position;

b) the second actuator displaces the movable stop to said open position;

c) the first actuator acts to impel the seals in the feed guide incrementally towards the reception and application station; and d) the second actuator displaces the movable stop) back to its seal application position.

The applicator pistol, according to the preferred embodiment of this aspect of the invention, allows rapid application of marking seals in series by pulling the trigger.

BRIEF DESCRIPTION OF THE DRAWINGS

The present invention will now be described in greater detail, by way of example, with reference to the accompanying drawings in which.

DETAILED DESCRIPTION OF THE INVENTION

Figure 1:
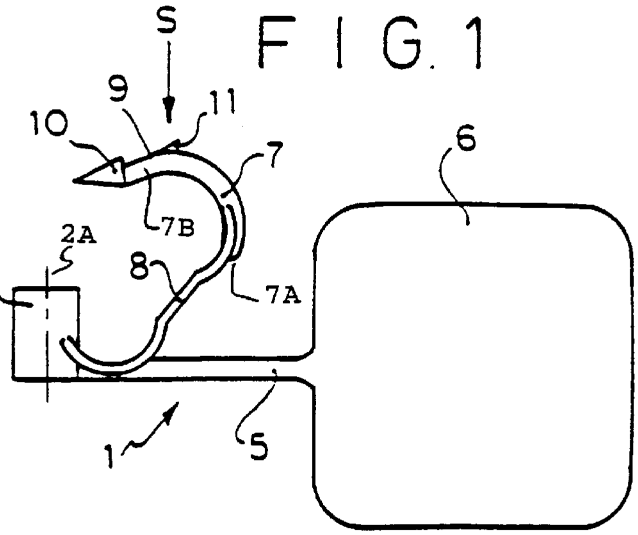
FIG. 1 is a plan view of a marking seal according to a first aspect of the present invention.
Figure 2:
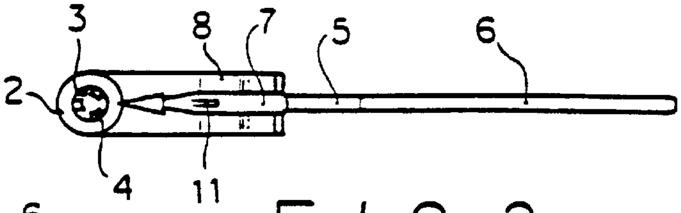
FIG. 2 is a lateral view of the seal shown in FIG. 1, looking in the direction of the arrow, S.

With reference to FIGS. 1 and 2 of the drawings, a padlock type marking seal 1 comprises a body 2 defining a cavity 3 containing a locking formation in the form of three internal teeth 4. A connection 5 joins a rectangular marking tab 6 to the body.

A loop 7 of seal 1, of transverse circular cross-section, is joined to the body at a first end 7*a* by an elongated region of smaller thickness that defines a folding or pivoting area 8 and comprises a substantially semicircular loop portion. A sharpened tip in the form of a head 9 has a neck which is joined to the second end 7*b* of the loop portion 7. With the object of ensuring that sharpened tip 9 does not flex, i.e. deflect, on penetrating the material to be marked, there is a rib 10 in the neck region. As shown in FIG. 1, the loop 7 and tip 9 are spaced form the axis 2*a* of cavity 2.

To close the seal, a force is exerted on the loop portion 7 toward the cavity axis. This moves the loop portion 7 and tip 9 outwardly to a position where the tip 9 enters cavity 3, the head catching behind locking teeth 4 and becoming locked, thereby defining a closed configuration of the seal. It should be observed that in this closed position rib 10 fits between two of the three locking teeth 4.

Slightly behind sharpened tip 9, at the end of the semicircular portion, there is a stop 11 in the shape of a barb to allow an applicator device to force sharpened tip 9 through the material to be marked, without an element of the device itself having to be sharpened in order to carry out the penetrating operation.

Figure 3:
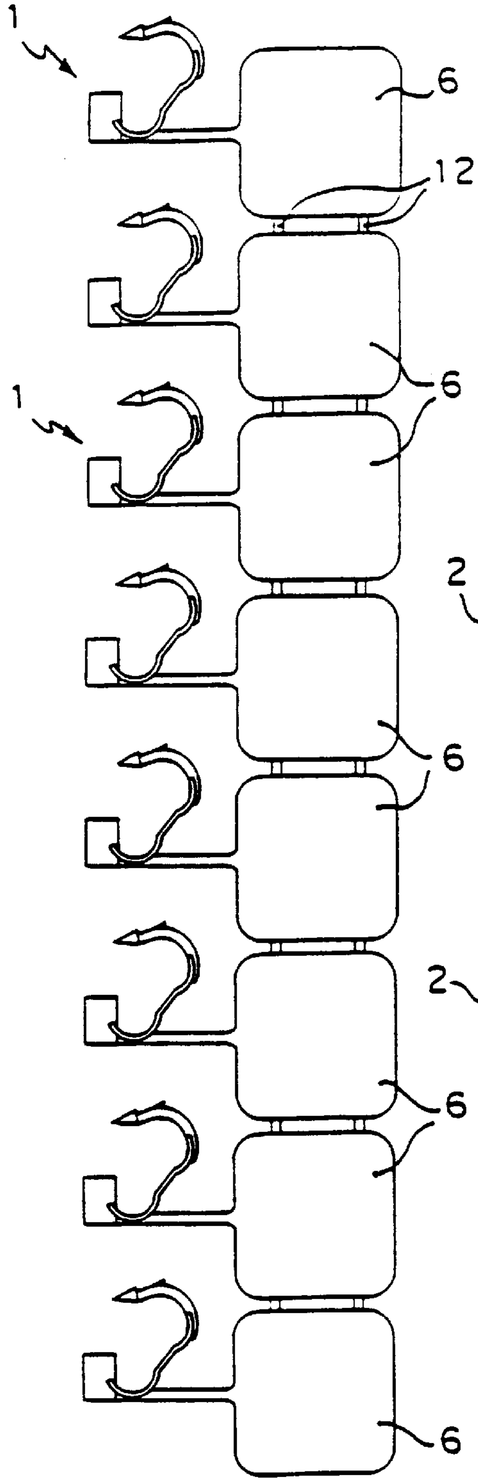
FIG. 3 is a plan view of a comb of marking seals for use in the applicator shown in FIGS. 4 to 6.

FIG. 3 shows a "comb" of seals 1, identical to the seal shown in FIGS. 1 and 2 with the exception that respective marking tabs 6 are joined to each other by two weakened points 12. A comb of seals such as that illustrated in FIG. 3 can be used with the applicator illustrated in FIGS. 4 to 6.

Figure 4:
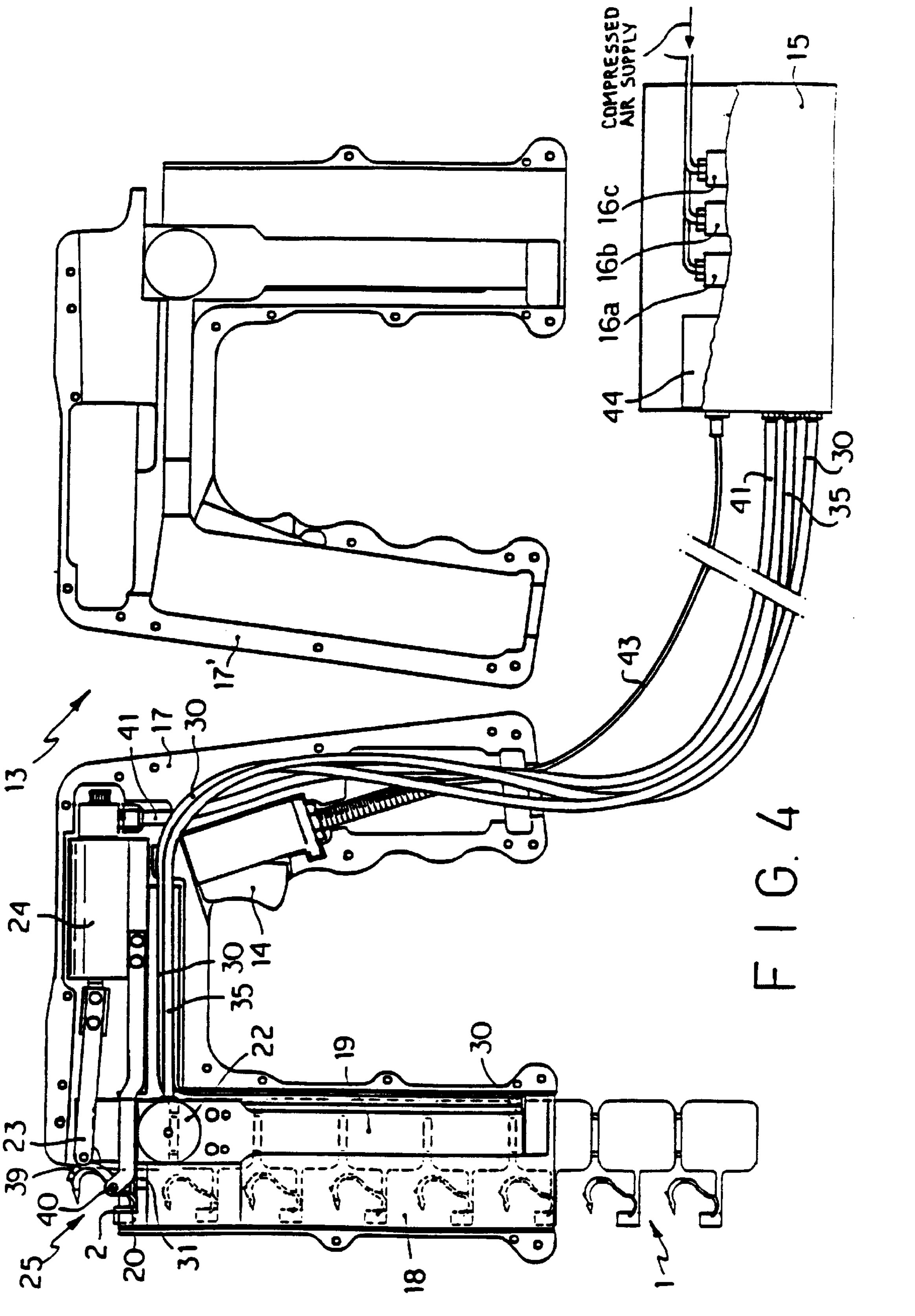
FIG. 4 is a plan view of a marking seal applicator according to the preferred embodiment of a second aspect of the invention, one half of the seal applicator having been removed to allow the interior of the applicator to be seen and showing a comb of seals similar to that illustrated in FIG. 3 with a first seal in position ready for application.
Figure 5:
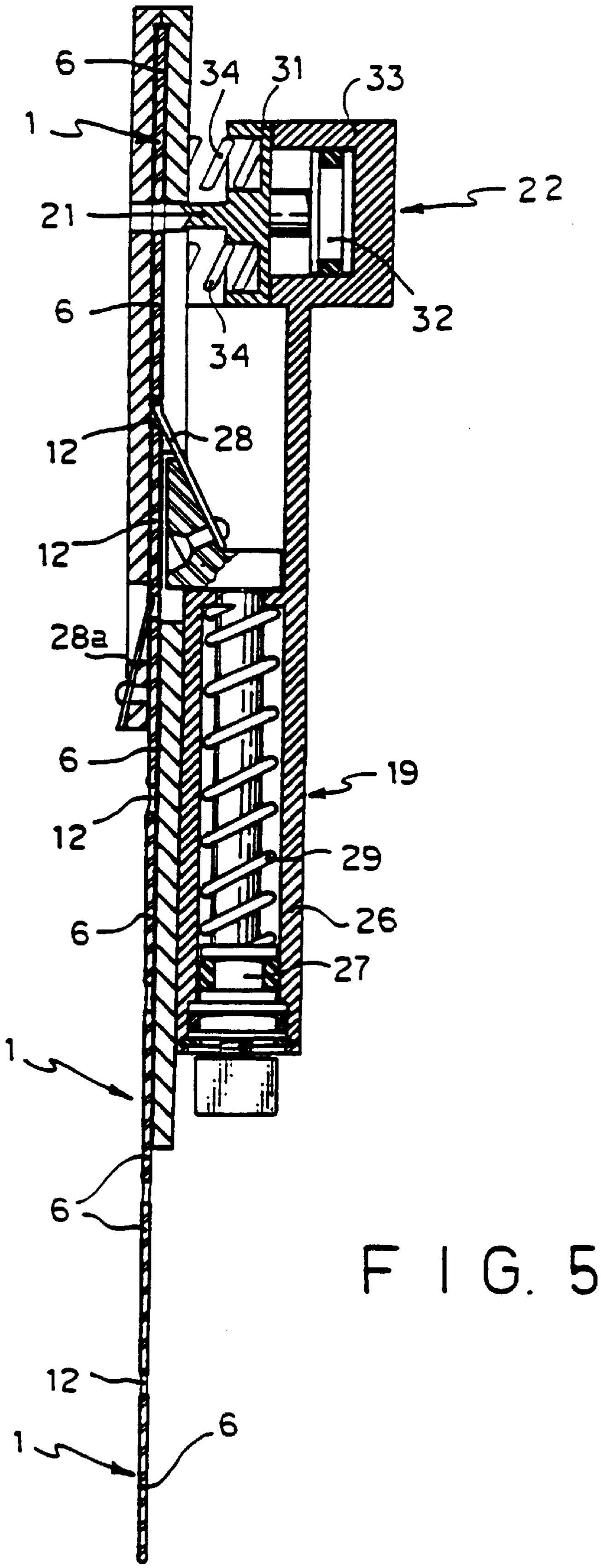
FIG. 5 is a longitudinal central cross sectional view of a pneumatic cylinder used to advance the seals in the applicator of FIG. 4, as well as of a pneumatic cylinder which actuates cutting pins and advances a movable stop to support the seals at the time of application.
Figure 6:
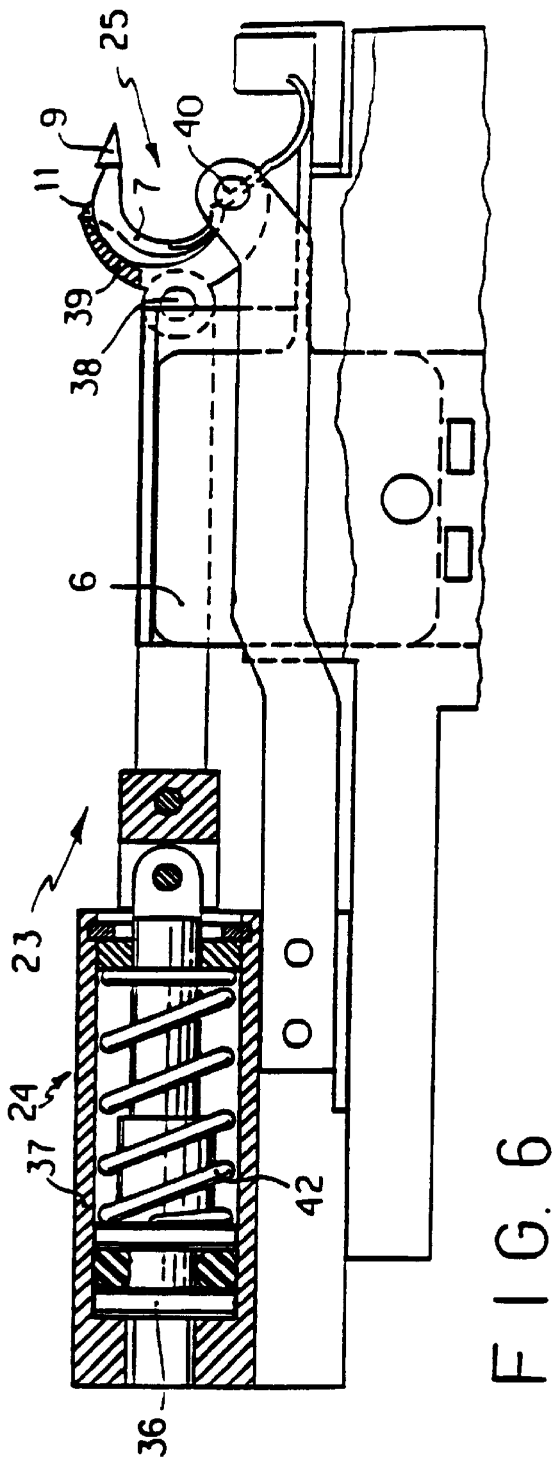
FIG. 6 is a longitudinal central cross sectional view of a seal actuator element, including a pneumatic cylinder for operating the actuator element.

Referring now to FIGS. 4 to 6, an applicator according to a preferred embodiment of the second aspect of the present invention comprises a pistol 13 having a trigger 14 and a programmed control unit 15 having pneumatic valves 16*a*, 16*b* and 16*c*.

Pistol 13 comprises a pistol mechanism housed in a chassis having two halves 17 and 17' joined together by screws. The pistol mechanism comprises a seal feed guide 18, a feed actuator 19, a movable stop 20, cutting pins 21 (FIG. 5) to sever weakened points 12 between adjacent seals (see FIG. 3), an actuator 22 for movable stop 20 and cutting pins 21, a seal applicator device 23 and an actuator 24 thereof.

Seal feed guide 18 receives the comb of seals 1 (FIG. 3), as illustrated, so that the seals can be fed towards a reception and application station 25. Feeding is carried out in incremental steps by means of feed actuator 19 which comprises a first pneumatic cylinder 26 including a piston 27 having a feed arm 28 that enters between marking tabs 6 of the upper two seals on the comb, a yieldable ratchet 28*a* that enters between the second and third seals on the comb to prevent the seals from dropping back after feeding, and a return spring 29 for piston 27. Pneumatic cylinder 26 is connected by a tube 30 to remote control unit 15 and more specifically to pneumatic valve 16*a*.

Movable stop 20 is integral with a plate 31, fixed to the end of the rod of a piston 32 of a second pneumatic cylinder 33 which forms actuator 22. Cutting pins 21 also project from plate 31. Springs 34 positioned between plate 31 and cylinder 33 laterally separate movable stop 20 from reception and application station 25 and cutting pins 21 from their cutting position. Cylinder 33 is connected by a tube 35 to pneumatic valve 16*b* in remote control unit 15 and, as will be described later, is normally subject to pneumatic pressure in order to keep movable stop 20 in the position illustrated. In such a position movable stop 20 obstructs the base of reception and application station 25 with the body 2 of the first seal 1 supported therein and ready for application. Movable stop 20 also restricts reception and application station 25 both laterally and in its forward region so as to ensure that the seal will not move either laterally or forwards during application.

Seal applicator device 23 (FIG. 6) comprises a pair of parallel bars 23' pivotally linked at first ends to a piston rod 36 of a third pneumatic cylinder 37 which forms actuator 24. Second ends of bars 23' are pivotally linked at two points 38 (laterally separated from each other) to a metal applicator element or cradle 39 in the form of an arc, the free end of which is pivoted about points 40, fixed with respect to chassis 17, 17' of the pistol. Cradle 39, having an internal surface that is semicircular in cross-section, receives loop 7 of seal 1 and the upper or forward point of the cradle abuts the rear surface of barb shaped stop 11 on the seal. The distance between fixed points 40 and the axis of cavity 3 of seal 1 in the reception and application station is substantially the same as the diameter of the semicircle described by loop 7 of the seal.

Thus, with a seal fed into reception and application station 25 as illustrated in FIG. 1, applying a pulse of compressed air to cylinder 37, supplied by pneumatic valve 16*c* and a tube 41, advances piston 36 against a return spring 42 causing bars 23' to move forward and rotate cradle 39 about a pivot axis corresponding to the line between fixed points 40. Such movement forces loop 7 of the seal in the reception and application station to pivot about its fold region 8, until tip 9 of the seal enters and becomes locked in cavity 3. It should be noted that cradle 39 ensures the alignment of loop 7 with cavity 3 of the seal during the closing operation, the position of body 2 of the seal being determined by movable stop 20.

Figure 7:
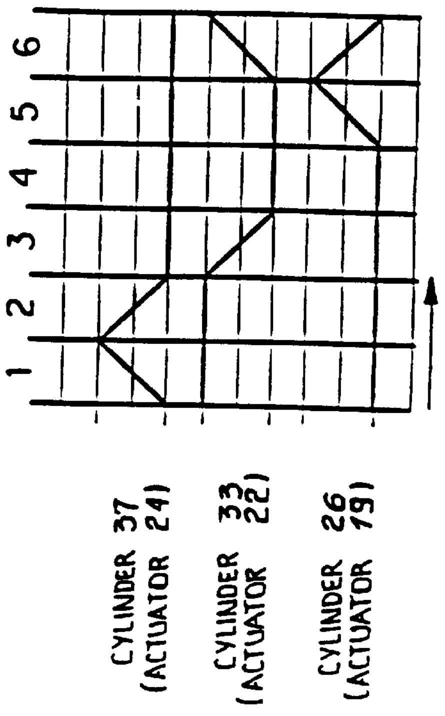
FIG. 7 is a graph showing the sequence of operations of the actuators and respective pneumatic cylinders of the applicator shown in FIGS. 4 and 6.

Operation of the marking seal applicator pistol is started by trigger 14 which is connected by an electrical connection 43 to an electronic circuit board 44 in programmed remote control unit 15. On pulling the trigger, circuit board 44 activates pneumatic valves 16*a*, 16*b* and 16*c* (these being connected to a supply of compressed air, not shown), according to the sequence of operations shown in FIG. 7, which are as follows:

a) providing a pulse of compressed air from pneumatic valve 16*c* to third pneumatic cylinder 37—as described above—causing application (closing) of seal 1, imeadiately after which valve 16*c* is closed and spring 42 returns applicator device 23 to its original, open seal, position;

b) closing second pneumatic valve 16*b*, to cut off the supply of pressure to second cylinder 33 of actuator 22 and thus allow springs 34 to move movable stop 20 and cutting pins 21 away from reception and application station 25, thereby leaving the lower part of station 25 free and open;

c) applying a pulse of compressed air, from first pneumatic valve 16*a*, to first feed cylinder 26 which, by means of piston 27 and arm 28, advances the next seal 1 in feed guide 18 into position within reception and application station 25. After this, return spring 29 returns both piston 27 and arm 28 to their initial positions ready for the next cycle to commence whilst ratchet 28*a* ensures that the seals do not move back down feed guide 18; and d) once again opening second pneumatic valve 16*b* thereby pressurizing second cylinder 33 and thus returning movable stop 20 back to its initial position. At the same time, cutting pins 21 return to their cutting positions thereby cutting weakened points 12 between the seal in reception and application station 25 and the adjacent seal which is still in feed guide 18.

During use, immediately after applying the seal and termination of step b) above, the pistol is moved away manually from the material being marked (a natural movement at this stage of the operation) and the seal, together with its marking tab 6, automatically leave the pistol permitting the sequence to be continued with steps c) and d). It should be noted that the free spaces between parallel bars 23' of applicator device 23 and between fixed rotation points 40 allow the unobstructed removal of the seal. On termination of the sequence a) to d) the pistol is already newly "armed" with the next seal in position for application.

It will be obvious that the marking seal applicator pistol described above, with reference to the attached drawings, permits the rapid application in series of as many seals as there are in the comb of seals carried in the pistol.

The operation is extremely easy, without requiring physical force, and the application is clean and reliable, thanks to the fact that applicator device 23 is not forced manually to penetrate the material to be marked (remaining behind sharpened tip 9 of the seal) and that tip 9 of the seal enters substantially rectilinearly into cavity 3. This is of utmost importance when marking comestible products, particularly meat. Note that, for this reason, the front end or tip of cradle 39, of applicator device 23, is champhered so as not to not create any influence on the material to be marked as it follows sharpened tip 9 of the seal.

The present invention is not limited to the preferred embodiments illustrated in the drawings. Many variations will be evident to those skilled in the art and the scope of the invention should therefore be limited only by the terms and interpretation of the following claims.

What is claimed is:

1. A padlock type marking seal, comprising:

a body defining a locking cavity having an internal formation and a cavity axis;

a substantially arcuate preformed loop portion having a first end and a second end;

a pivot portion weakened relative to said loop portion and connecting said first end of said loop portion to said body;

a barb formed on said loop portion, said barb having a leading end substantially at said second end of said loop portion; and a sharp piercing tip integral with and extending tangentially beyond said second end of said loop portion, said tip having a tip axis, and wherein said tip is in the form of a head connected to said second end of said loop portion by a neck, there being a reinforcement in the form of a connecting rib in the vicinity of said neck, said tip and said loop portion being spaced from said cavity axis;

said pivot portion supporting said loop portion and said tip in a seal open position remote from said cavity and for movement toward said cavity axis, in response to force exerted on said barb toward said cavity axis, to a position where said tip enters said cavity along said cavity axis.

2. Marking seal applicator for applying padlock type marking seals in which a tip of a preformed loop of the seal is sharpened so as to penetrate the material to be marked and, upon exiting the other side of the material, to enter into a locking cavity of the seal, said applicator including a seal reception and application station, a seal applicator device at said reception and application station for rotation about a pivot point, and actuator means for inserting said tip into said locking cavity, the marking seal applicator comprising:

a feed guide defining a pathway for feeding a series of interconnected seals toward said reception and application station, a region of the reception and application station being open to the feed guide so as to enable a marking seal to pass from the guide into a reception and application position within said reception and application station;

a movable stop, displaceable between an open position, spaced from the reception and application station, and a seal application position in which the movable stop is located in said open region to align and support that portion of the seal defining said locking cavity; and a first actuator for advancing the seals incrementally along the feed guide toward the reception and application station, said actuator means comprising a second actuator for displacing said stop between said open and seal application positions, and a third actuator for imparting rotational motion thereto, between an open seal position and a closed seal position, and for returning said applicator device to said open seal position;

said applicator device including an actuator element having an inner curved surface adapted to substantially correspond to a shape of an outer surface of said preformed loop of a seal located in the reception and application station, with the sharpened tip of the loop of the seal directed away from the applicator device, the applicator device adapted to cooperate with the loop so as to move together with the applicator when it is rotated about the pivot point by said third actuator.

3. Marking seal applicator according to claim 2, wherein said first, second and third actuators comprise respective first, second and third pneumatic cylinders with return springs.

4. Marking seal applicator according to claim 3, wherein the marking seal applicator is in the form of a pistol with a trigger for starting an operating sequence of said actuators.

5. Marking seal applicator according to claim 4, further comprising a remote control unit, including pneumatic valves for controlling an application of pneumatic pressure to said cylinders, and an electronic circuit programmed to open and close said valves according to said actuator operation sequence, the electronic circuit being activated by the trigger of the pistol.

6. Marking seal applicator according to claim 5, wherein said remote control unit is programmed so that, upon pulling said trigger, said operating sequence occurs as follows:

(a) the third actuator rotates the applicator device from its open seal position into the closed seal position and soon after back to the open seal position;

(b) the second actuator displaces the movable stop to said open position;

(c) the first actuator acts to impel the seals in the feed guide incrementally toward the reception and application station; and (d) the second actuator displaces the movable stop back to its seal application position.

7. Marking seal applicator device according to claim 2, further comprising a cutting mechanism, adjacent said open region of the reception and application station, for cutting weakened links between adjacent seals in said series, the cutting mechanism being operable so as to effect cutting simultaneously with displacement of said movable stop to the seal application position.

8. A combination, comprising: a padlock type marking seal and a marking seal applicator, wherein said padlock type marking seal comprises:

a body defining a locking cavity having an internal formation and a cavity axis;

a substantially arcuate preformed loop portion having a first end and a second end;

a pivot portion weakened relative to said loop portion and connecting said first end of said loop portion to said body;

a barb formed on said loop portion, said barb having a leading end substantially at said second end of said loop portion; and a sharp piercing tip integral with and extending tangentially beyond said second end of said loop portion, said tip having a tip axis, said tip and said loop portion being spaced from said cavity axis;

said pivot portion supporting said loop portion and said tip in a seal open position remote from said cavity and for movement toward said cavity axis, in response to force exerted on said barb toward said cavity axis, to a position where said tip enters said cavity along said cavity axis, and wherein said marking seal applicator comprises:

a seal reception and application station, a seal applicator device at said reception and application station for rotation about a pivot point, and actuator means for inserting said tip into said locking cavity;

a feed guide defining a pathway for feeding a series of interconnected seals toward said reception and application station, a region of the reception and application station being open to the feed guide so as to enable a marking seal to pass from the guide into a reception and application position within said reception and application station;

a movable stop, displaceable between an open position, spaced from the reception and application station, and a seal application position in which the movable stop is located in said open region to align and support that portion of the seal defining said locking cavity;

said actuator means comprising a first actuator for advancing the seals incrementally along the feed guide toward the reception and application station; a second actuator for displacing said movable stop between said open and seal application positions; and a third actuator for imparting rotational motion to said applicator device, between an open seal position and a closed seal position, and for returning said applicator device to said open seal position;

said applicator device including an actuator element having an inner curved surface substantially corresponding to a shape of an outer surface of said preformed loop portion of a seal located in the reception and application station, with the sharp tip of the loop of the seal directed away from the applicator device, the applicator device cooperating with the loop portion so as to move together with the applicator when it is rotated about the pivot point by said third actuator.

9. The combination according to claim 8, wherein said first, second and third actuators include respective firs second and third pneumatic cylinders with return springs.

10. The combination according to claim 9, wherein the applicator is in the form of a pistol with a trigger for starting an operating sequence of said actuators.

11. The combination according to claim 10, further comprising a remote control unit including pneumatic valves for controlling an application of pneumatic pressure to said cylinders, and an electronic circuit programmed to open and close said valves according to said actuator operation sequence, the electronic circuit being activated by the trigger of the pistol.

12. The combination according to claim 11, wherein said remote control unit is said trigger, said operating sequence occurs as follows:

(a) the third actuator rotates the applicator device from its open seal position into the closed seal position and soon after back to the open seal position;

(b) the second actuator displaces the movable stop to said open position;

(c) the first actuator acts to impel the seals in the feed guide incrementally toward the reception and application station; and (d) the second actuator displaces the movable stop back to its seal application position.

13. The combination according to claim 8, further comprising a cutting mechanism, adjacent said open region of the reception and application station, for cutting weakened links between adjacent seals in said series, the cutting mechanism being controlled by the second actuator so as to effect cutting simultaneously with displacement of said movable stop to the seal application position.

* * * * *